(12) United States Patent
Wu

(10) Patent No.: US 8,299,244 B1
(45) Date of Patent: Oct. 30, 2012

(54) MELAMINE COMPOUND AND METHOD FOR MANUFACTURING THE SAME

(75) Inventor: Hsin-Ho Wu, Chupei (TW)

(73) Assignee: Taiwan Union Technology Corporation, Chupei (TW)

( * ) Notice: Subject to any disclaimer, the term of this patent is extended or adjusted under 35 U.S.C. 154(b) by 0 days.

(21) Appl. No.: 13/205,944

(22) Filed: Aug. 9, 2011

(30) Foreign Application Priority Data

Jun. 22, 2011 (TW) .............................. 100121790 A

(51) Int. Cl.
C07D 413/14 (2006.01)
C07D 403/14 (2006.01)
C07D 265/14 (2006.01)
A61K 31/53 (2006.01)
A61K 31/536 (2006.01)

(52) U.S. Cl. ........................................ 544/198; 544/196

(58) Field of Classification Search ................. 544/198, 544/196
See application file for complete search history.

(56) References Cited

U.S. PATENT DOCUMENTS 7,781,561 B2  8/2010 Lin et al.

*Primary Examiner* — Venkataraman Balasubramanian
(74) *Attorney, Agent, or Firm* — Grossman, Tucker, Perreault & Pfleger, PLLC

(57) ABSTRACT

A melamine derivative of Formula I and its preparing method are provided:

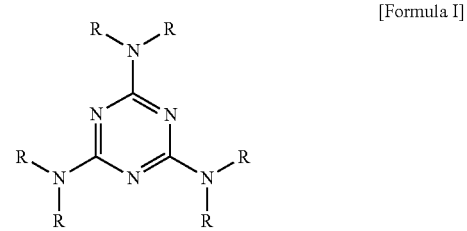

[Formula I]

wherein,
R is the same with or different from each other and has the formula of

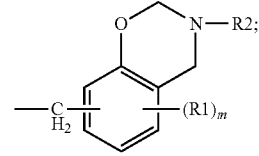

R1 and R2 are independently selected from a group consisting of H, a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group, with a proviso that R2 is not H; and
m is 1 or 2.

12 Claims, 2 Drawing Sheets

MELAMINE COMPOUND AND METHOD FOR MANUFACTURING THE SAME

This application claims priority to Taiwan Patent Application No. 100121790 filed on Jun. 22, 2011.

CROSS-REFERENCES TO RELATED APPLICATIONS

Not applicable.

BACKGROUND OF THE INVENTION

1. Field of the Invention

The present invention relates to a melamine compound and its manufacturing method.

The melamine compound can be used as a hardener for epoxy resin.

2. Descriptions of the Related Art

Printed circuit boards (PCBs) are circuit substrates that are used for electronic devices to load other electronic components and to electrically connect the components to provide a stable circuit working environment. One kind of a conventional printed circuit board is a copper clad laminate (CCL), which is primarily composed of resin(s), reinforcing material(s) and copper foil(s). Conventional resins include such as epoxy resins, novolac resins, polyamine formaldehyde resins, silicone resins or polytetrafluoroethylene resins; and conventional reinforcing materials include such as glass fiber cloths, glass fiber mats, insulating papers or linen cloths.

Considering the subsequent electronic processes, properties such as heat resistance, size stability, chemical stability, workability, toughness, and mechanical strength etc. should be taken into consideration during the preparation of the printed circuit board. Generally, printed circuit broads prepared by using an epoxy resin can properly meet the above requirements. Hence, epoxy resins are those most commonly used in this field. However, printed circuit broads prepared by using an epoxy resin are usually provided with a high dielectric constant (Dk) value and a high dissipation factor (Df) value, which are disadvantageous to the signal transmission. Specifically, because the signal transmission rate is in inverse proportion to the square root of Dk, the higher the Dk value the lower the signal transmission rate; and due to the material resistance, the higher the Df value the higher the signal lost in the laminate. Therefore, the industry is committed to provide a laminate with good physicochemical properties and low Dk and Df values.

It is known that N,O-heterocyclic compounds with a

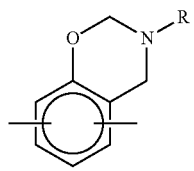

structure can be used as a hardener to regulate epoxy resin. Due to the high proportion of benzene rings and C—N bonds in the structure, the N,O-heterocyclic compounds possess excellent physicochemical properties (such as a good thermal resistance, a high glass transition temperature, an outstanding flammability and a good solubility for organic solvents). In addition, the polymer prepared from a ring-opening polymerization of N,O-heterocyclic compounds has a large number of hydroxyl groups in its structure and can further react with an epoxy resin to provide a final product with improved thermal and mechanical properties. For example, U.S. Pat. No. 7,781,561 discloses a method for manufacturing an N,O-heterocyclic compound with a

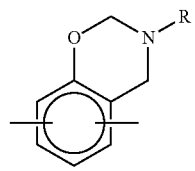

structure, wherein a melamine compound with three

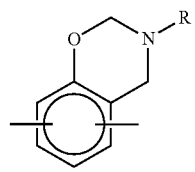

structures is synthesized with the utilization of a melamine.

The present invention provides a novel melamine compound with a high proportion of

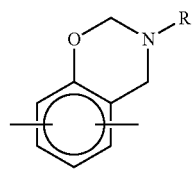

structure. The melamine compound is provided with outstanding physicochemical properties, and when being used as a hardener of epoxy resin for preparing PCBs, it can effectively lower the Df of the PCBs.

SUMMARY OF THE INVENTION

An aspect of the present invention is to provide a melamine compound of Formula I:

[Formula I]

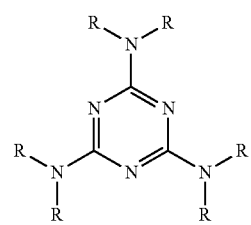

wherein,
R is the same with or different from each other and has the formula of

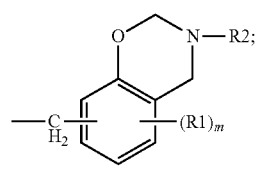

R1 is independently selected from a group consisting of H, a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group;

R2 is selected from a group consisting of a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group; and m is 1 or 2.

Another aspect of the present invention is to provide a method for manufacturing a melamine compound, the method comprises:

(a) reacting melamine with formaldehyde under a basic condition to provide a first solution;

(b) reacting the first solution with a phenolic compound of Formula Ia to provide a first intermediate:

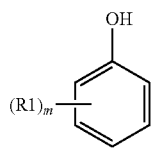

[Formula Ia]

(c) reacting the first intermediate with formaldehyde and a primary amine having a general formula of $NH_2R2$ to obtain the melamine compound, wherein, R1 is independently selected from a group consisting of H, a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group;

R2 is selected from a group consisting of a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group; and m is 1 or 2.

To render the above objects, technical features and advantages of the present invention more apparent, the present invention will be described in detail with reference to some embodiments hereinafter.

DESCRIPTION OF THE PREFERRED EMBODIMENT

Figure 1:
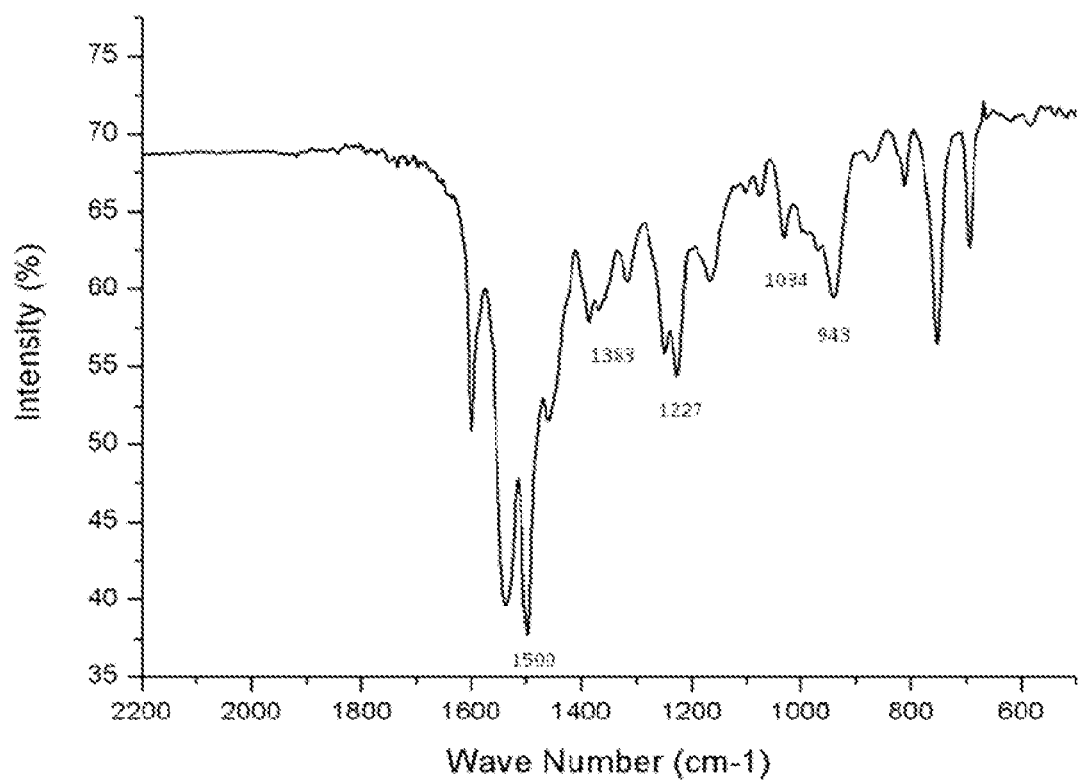
FIG. 1 shows the IR spectrum of the melamine compound of the present invention illustrated in the examples.

The following will describe some embodiments of the present invention in detail. However, without departing from the spirit of the present invention, the present invention may be embodied in various embodiments and should not be limited to the embodiments described in the specification. In addition, unless it is additionally explained, the expressions "a," "the," or the like recited in the specification (especially in the claims) should include the singular and the plural forms.

The present invention provides a melamine compound and a method for manufacturing the same. Due to the high proportion of benzene rings and C—N bonds in the structure (six

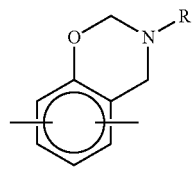

structures per molecule), the melamine compound possesses excellent physicochemical properties (such as thermal resistance, moisture resistance and electrical property). Thus, the polymer prepared from a ring-opening polymerization of the melamine compound has a larger number of hydroxyl groups and can further react with an epoxy resin to improve the thermal and mechanical properties of final products.

Specifically, the invention provides a melamine compound of Formula I:

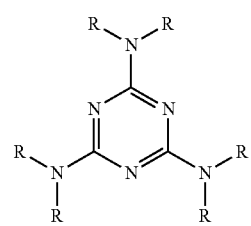

[Formula I]

wherein, R is the same with or different from each other and has the formula

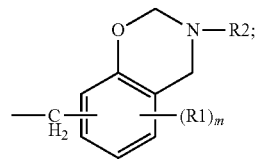

of R1 is independently selected from a group consisting of H, a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group; R2 is selected from a group consisting of a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group; and m is 1 or 2. For example, R1 and R2 may be independently methyl, ethyl, propyl, butyl, methoxyl, ethoxyl or a substituted or unsubstituted phenyl or phenoxy group. The term "substituted" here means that H is substituted by a substituent which can be any groups or atoms other than "H." For example, the substituent may be a halogen (such as F or Cl), a hydroxyl, a cyano, a carboxyl, an alkyl, an epoxy or an alkoxy. Without being limited by any theories, it is believed that the higher the proportion of benzene rings and unsaturated bonding in the melamine compound, the better the thermal and the mechanical and chemical properties of the final product. Thus, R1 and R2 are preferably independently a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, or a dicyclopentadiene group. In some embodiments of the present invention, R is the same with each other, R1 is H and R2 is a substituted or unsubstituted phenyl group. As illustrated in the following examples, the melamine compound of the present invention can be used in an epoxy resin composition as a hardener.

The present invention further provides a method for manufacturing the melamine compound, the method comprises:

(a) reacting melamine with formaldehyde under a basic condition to provide a first solution;

(b) reacting the first solution with a phenolic compound of Formula Ia to provide a first intermediate:

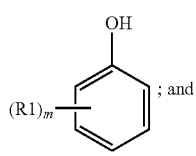

[Formula Ia]

; and (c) reacting the first intermediate with formaldehyde and a primary amine having a general formula of NH$_2$R2 to obtain the melamine compound.

Without being limited by any theories, it is believed that the following reaction is performed in step (a) to provide the first solution comprising compound A:

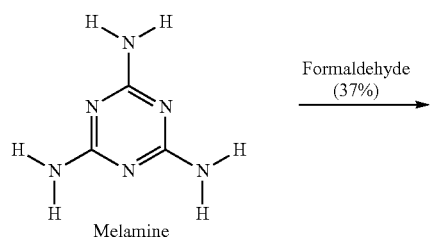

Melamine

Formaldehyde (37%)

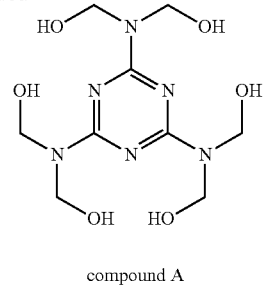

compound A

The above reaction must be carried out in a basic condition (preferably at a pH value ranging from about 8 to about 10) and at a temperature ranging from about 50° C. to about 75° C. It is disadvantageous to the yield of compound A if the pH value is unduly high (such as >10) or the temperature goes beyond the preferred range. In some embodiments of the present invention, step (a) is carried out at about 60° C. to about 65° C. and at a pH value ranging from about 8 to about 9.

Without being limited by any theories, it is believed that OH group of compound A reacts with the phenolic compound of Formula Ia in step (b) to perform a dehydration reaction to form the first intermediate, as shown in the following equation:

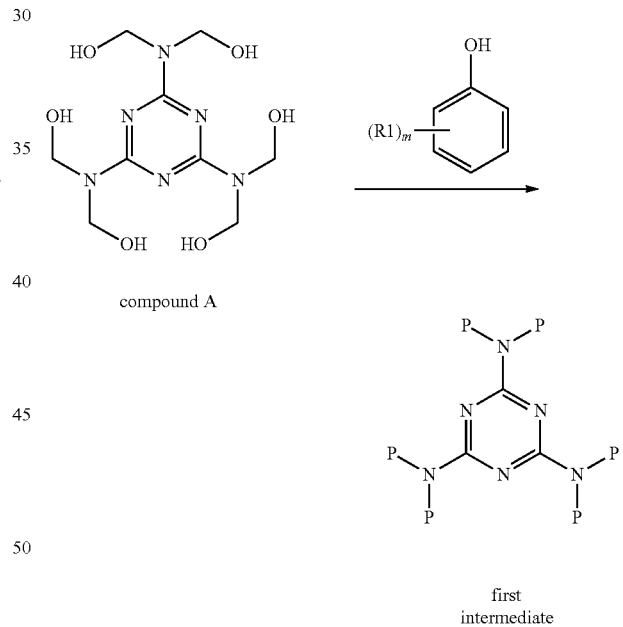

compound A first intermediate wherein, P is

R1 is independently selected from a group consisting of H, a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group; and m is 1 or 2. For example, R1 may be methyl, ethyl, propyl, butyl, methoxyl, ethoxyl or a substituted or unsubstituted phenyl or phenoxy group. Without being limited by any theories, it is believed that the higher the proportion of benzene rings and unsaturated bonding in the melamine compound, the better the thermal and the mechanical and chemical properties of the final product. Thus, R1 is preferably a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, or a dicyclopentadiene group.

To raise the yield of the melamine compound of the present invention, it is preferred that the pH value of the first solution is adjusted to neutral prior to step (b) and that step (b) is carried out at a temperature ranging from about 80° C. to about 95° C. Optionally, a purifying step and drying step may be carried out after step (b) to extract the first intermediate to improve the purity of the first intermediate and to obtain a melamine compound with better quality after step (c). For example, in some embodiments of the present invention, the method comprises adjusting the pH value of the first solution to neutral by using phosphoric acid; carrying out the reaction of step (b) at about 95° C.; mixing the product of step (b) with Water to form an emulsion; and purifying the emulsion by MEK/Water and drying the emulsion to obtain the first intermediate, a white solid product.

Without being limited by any theories, it is believed that the phenyl of the first intermediate is reacted with formaldehyde and the primary amine in step (c) to form the melamine compound of the present invention, as shown in the following reaction:

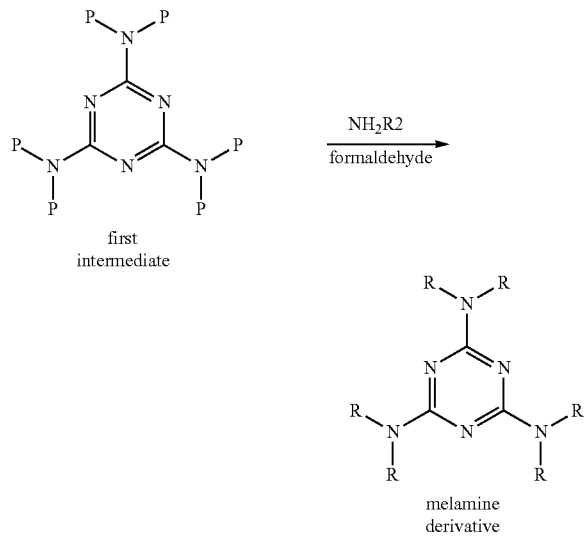

wherein, P and R are as defined above; R2 is selected from a group consisting of a halogen, a substituted or unsubstituted C1-C15 alkyl, a substituted or unsubstituted C1-C15 alkoxy, a substituted or unsubstituted C3-C15 cycloalkyl, a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, and a dicyclopentadiene group; and m is 1 or 2. For example, R2 may be methyl, ethyl, propyl, butyl, methoxyl, ethoxyl or a substituted or unsubstituted phenyl or phenoxy group. Without being limited by any theories, it is believed that the higher the proportion of benzene rings and unsaturated bonding in the melamine compound, the better the thermal and the mechanical and chemical properties of the final product. Thus, R2 is preferably a substituted or unsubstituted C6-C20 aryl, a substituted or unsubstituted C6-C20 aryloxy, a substituted or unsubstituted C1-C15 unsaturated hydrocarbyl, a naphthol group, a phenanthrenol group, or a dicyclopentadiene group.

Furthermore, to raise the yield of the melamine compound of the present invention, step (c) is preferably carried out in the following manner:

mixing the first intermediate with the solvent and the primary amine having a general formula of $NH_2R2$ to provide a first reaction mixture;

adding formaldehyde into the first reaction mixture and carrying out a reaction at a temperature ranging from about 80° C. to about 95° C. to obtain a solution containing the melamine compound; and purifying and drying the solution to obtain the melamine compound.

For example, in some embodiments of the present invention, the first intermediate and aniline were dissolved into a solvent such as dioxane to provide the first reaction mixture, and formaldehyde was then added dropwise into the first reaction mixture. The resultant mixture was heated to about 90° C. and maintained to carry out the reaction. After the reaction is completed, the solvent was removed by vacuum concentration to obtain the crude product of melamine compound. The crude product was then purified by MEK/DI-water and dried to obtain the melamine compound of the present invention. The solvent here should be an inert solvent which does not affect the reaction. And if the primary amine is in the form of a liquid at room temperature, the solvent may not be used. For example, the solvent may be an inert solvent selected from a group consisting of dioxane, toluene, xylene, N,N-dimethyl formamide (DMF), N,N-dimethyl acetamide (DMAc), dimethyl sulfoxide (DMSO) and combinations thereof.

The present invention will be further illustrated by the embodiments hereinafter, wherein the measuring instruments and methods are respectively as follows:

[Nuclear Magnetic Resonance (NMR) Analysis]

NMR spectrometer of Variun company (model No.: Mercury-VX200 MHz).

[Infrared Spectroscopic Analysis]

Infrared spectrometer of Bio-RAD company (model No.: FTS-3000).

[Differential Scanning Calorimetry (DSC) Analysis]

Differential scanning calorimeter of Perkin-Elmer company (model No.: DSC 7).

[Gel Permeation Chromatography (GPC) Analysis]

Gel permeation chromatography analyzer of Waters company (model No.: waters 600).

[Glass Transition Temperature (Tg) Test]

The glass transition temperature is measured by a dynamic mechanical analyzer (DMA), wherein the measuring regulations are IPC-TM-650.2.4.25C and 24C testing method of Institute for Interconnecting and Packaging Electronic Circuits (IPC).

[Dielectric Constant (Dk) and Dissipation Factor (Df) Measurement]

Dk and Df are measured according to ASTM D150 under an operating frequency of 1 GHz.

[H₂O Absorption Test]

The H₂O absorption of the laminate is tested by pressure cooker test (PCT), i.e., subjecting the laminate into a pressure container (121° C., 100% R.H. and 1.2 atm) for 2 hr.

[Coefficient of Thermal Expansion (CTE) Test and Z-axis Expansion Percentage (%) test]

The through-thickness CTE (in z-axis direction) and the z-axis expansion % of the sample (a laminate in a size of 3 mm²) are tested by the thermal expansion analyzer of TA instrument company (model No.: TA 2940) between a temperature gap ranging from about 50° C. to 260° C. (heating rate: 5° C./min).

[Thermal Decomposition Temperature Test]

The thermal decomposition temperature test is carried out by measuring the mass loss of the sample with a thermogravimetric analyzer (TGA). The temperature where the mass loss is up to 5% is regarded as the thermal decomposition temperature.

[Toughness Test]

The method for testing the toughness comprises the following steps: laying the laminate on a plane fixture; vertically placing a cross metal jig to come into contact with the surface of the laminate while applying a vertically-applied pressure to the cross metal jig; removing the cross metal jig; and observing the cross trace on the substrate. The laminate without any white embossing lines is regarded as having good toughness, the one with slight white embossing lines is regarded as having normal toughness, and the one with cracks or rupturing one is regarded as having poor toughness.

[Flammability Test]

The flammability test is carried out according to UL94V (Vertical Burn), which comprises the burning of a laminate, which is held vertical, using a Bunsen burner to obtain its self-ignition and combustion-supporting properties. The result is classified from UL94V-0 (the best) to UL94V-2.

EXAMPLES

The Preparation of the Melamine Compound

Melamine 126 g (1 mole) and 37% formaldehyde 487.0 g (6 moles) were placed in a 5 liter reactor, which was equipped with a stirrer and a condenser, and uniformly mixed to obtain a mixture. The pH of the mixture was adjusted to about 8 to about 9 by a 10% NaOH solution. The mixture was then heated and stirred to about 60° C. to about 65° C. and maintained for 40 minutes to complete the displacement reaction to form the first solution. The first solution was cooled down to room temperature and neutralized by an 85% H₃PO4 solution.

Phenol 2820 g (30 moles) and 0.001 mole p-toluene sulfonic acid (pTSA) were added to the first solution. The resultant mixture is then heated and stirred to about 95° C. and maintained for 24 hours. Thereafter, the reactor was cooled down to room temperature and 5 liters DI-water was poured thereinto. After stirring for a few hours, the colloidal crude product of the first intermediate was obtained. The colloidal crude product was then washed with DI-water for few times, purified by MEK/DI-water, and filtered and dried to obtain a white solid of the first intermediate.

760 g (1 mole) first intermediate, 558 g (6 moles) aniline and 2000 ml dioxane were placed into a 5 liter reactor, which was equipped with a stirrer and a condenser, and uniformly mixed to obtain a mixture. The mixture was maintained at about 0° C. to about 5° C. while 974 g (12 moles) 37% formaldehyde was added dropwise to the mixture. Thereafter, the mixture was heated and stirred to about 90° C. and maintained for 24 hours. Then, the solvent was removed through a rotary evaporator to obtain a light yellow crude product. The crude product was purified by MEK/DI-water to obtain the light yellow product of melamine compound A.

The Proton NMR spectra ($d_6$-DMSO) of melamine compound A shows the characteristic signal of benzoxazine at about 4.5 and about 5.4 ppm, and the aromatic protons around about 6.5 to about 8.0 ppm.

As shown in FIG. 1, which shows the IR spectrum of melamine compound A, there are characteristic absorptions of —COC— group at about 1034 cm⁻¹ and about 1227 cm⁻¹, —CNC— group at about 1383 cm⁻¹, and the absorption at about 943 cm⁻¹ and about 1500 cm⁻¹ are attributed to tri-substituted benzene ring.

Figure 2:
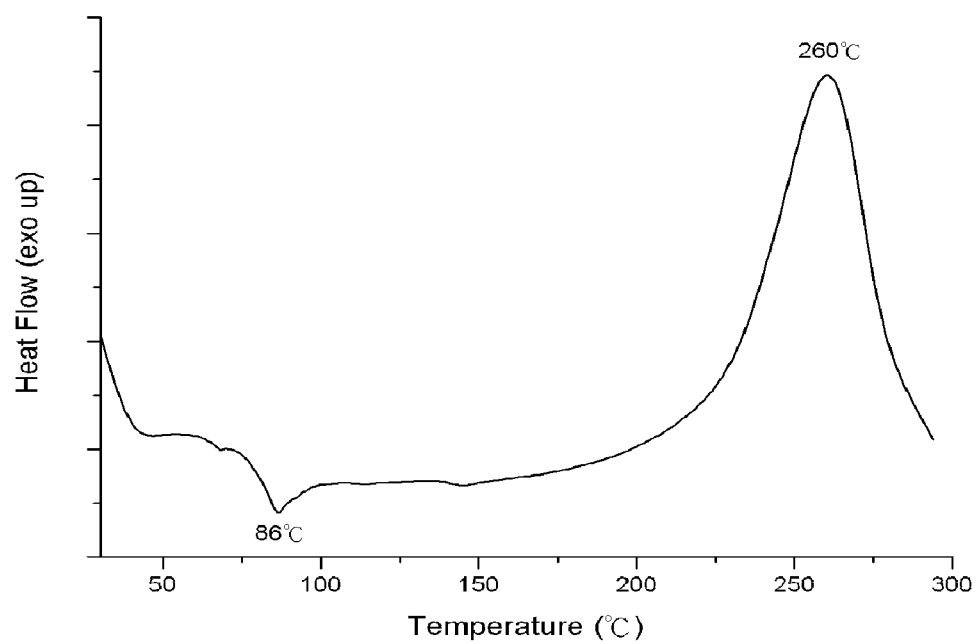
FIG. 2 shows the differential scanning calorimetry (DSC) analysis result of the melamine compound of the present invention illustrated in the examples.
Figure 3:
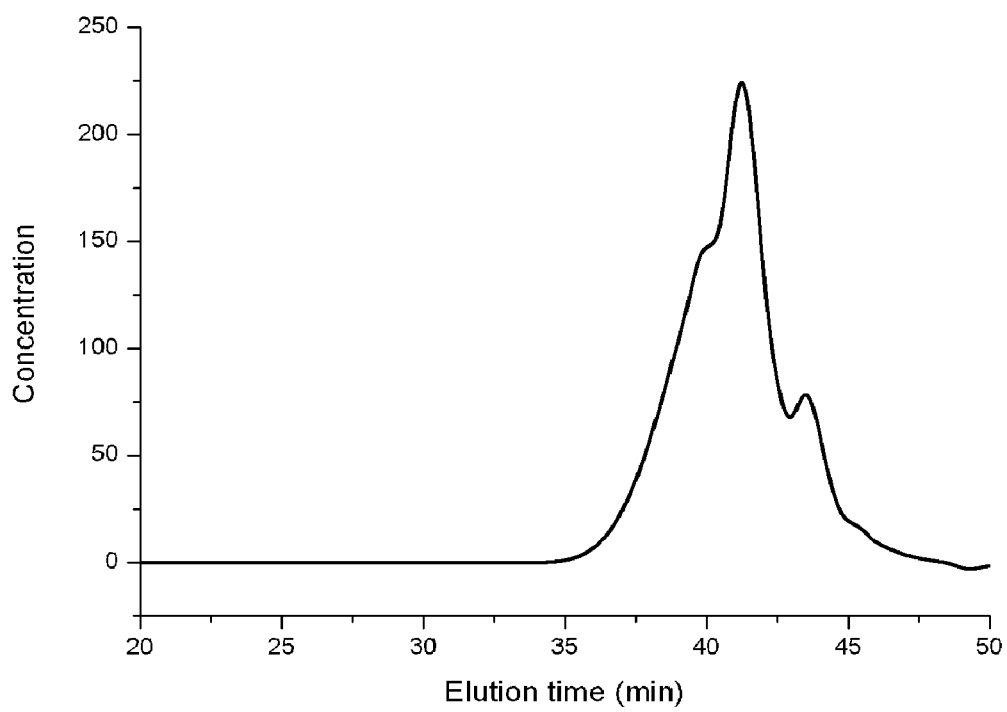
FIG. 3 shows the gel permeation chromatography (GPC) analysis result of the melamine compound of the present invention illustrated in the examples.

As shown in FIG. 2, which shows the DSC analysis (scan rate: 20° C./min) result of melamine compound A, the melting point of melamine compound A is about 86° C. and the temperature of ring-open reaction of melamine compound A is about 260° C. As shown in FIG. 3, which shows the GPC analysis result of melamine compound A, the weight-average molecular weight (Mw) of melamine compound A is about 1872 and the number-average molecular weight (Mn) of melamine compound A is about 1243 (polydispersity=1.50; elution solvent: THF).

[The Preparation of the Printed Circuit Broad]

High bromine epoxy resin (Hexion 523), melamine compound A, 2-methylimidazole (2-MI) and MEK were uniformly mixed under room temperature in the ratio of Table 1 to obtain resin composition A.

Resin composition A was coated on a plurality of 7628 glass fiber cloths (resin/glass fiber cloth: 43%) by a roll coater. The coated 7628 glass fiber cloths were then placed in a dryer and dried at 180° C. for 2 to 5 minutes to prepare prepregs in half-hardened state. Eight pieces of the prepregs were superimposed and two copper foils were respectively superimposed on the two external surfaces of the superimposed prepregs to provide a superimposed object. A hot-pressing operation was performed onto the superimposed object to provide a copper clad laminate A, wherein the hot-pressing conditions are as follows: raising the temperature to 180° C. with a heating rate of 2.0° C./min, and hot-pressing for 90 minutes under the full pressure of 15 kg/cm² (the initial pressure is 8 kg/cm²) at 180° C. The glass transition temperature (Tg), dielectric constant (Dk), dissipation factor (Df), H₂O absorption, coefficient of thermal expansion (CTE), z-axis expansion (%), thermal decomposition temperature, toughness and flammability of copper clad laminate A were analyzed and the results were shown in Table 2.

TABLE 1

|  | high bromine epoxy resin (parts by weight) | melamine compound A (parts by weight) | 2-MI (parts by weight) | MEK (parts by weight) |
|---|---|---|---|---|
| resin composition A | 100 | 80 | 0.1 | 100 |

TABLE 2

|  | Laminate A |
|---|---|
| Tg (° C.) | 205 |
| Dk (1 GHz) | 3.90 |
| Df (1 GHz) | 0.009 |

TABLE 2-continued

|  | Laminate A |
|---|---|
| H$_2$O absorption (%) | 0.25 |
| CTE (ppm/° C.) | 35 |
| z-axis expansion (%) | 3.0 |
| thermal decomposition temperature (° C.) | 384 |
| toughness test | good |
| UL94 (Grade) | V0 |

As shown in Table 2, the melamine compound of the invention can be used as a hardener for epoxy resin, and the laminate manufactured thereby is provided with outstanding heat resistance (e.g., a high Tg), moisture resistance (a low H$_2$O absorption) and electrical properties (low Dk and Df).

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A melamine compound of Formula I:

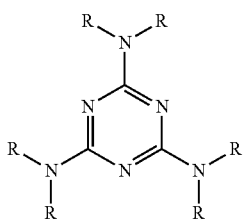

[Formula I]

wherein,
R is the same with or different from each other and has the formula of

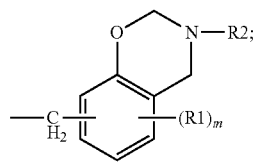

R1 is independently selected from a group consisting of H; a C1-C15 alkyl unsubstituted or substituted by an alkyl or an alkoxy; a C1-C15 alkoxy unsubstituted or substituted by an alkyl or an alkoxy; a C3-C15 cycloalkyl unsubstituted or substituted by an alkyl or an alkoxy; a C6-C20 aryl unsubstituted or substituted by an alkyl or an alkoxy; a C6-C20 aryloxy unsubstituted or substituted by an alkyl or an alkoxy; and a dicyclopentadiene group;

R2 is selected from a group consisting of a C1-C15 alkyl unsubstituted or substituted by an alkyl or an alkoxy; a C1-C15 alkoxy unsubstituted or substituted by an alkyl or an alkoxy; a C3-C15 cycloalkyl or unsubstituted or substituted by an alkyl or an alkoxy; a C6-C20 aryl or unsubstituted or substituted by an alkyl or an alkoxy; a C6-C20 aryloxy unsubstituted or substituted by an alkyl or an alkoxy; and a dicyclopentadiene group; and m is 1 or 2.

2. The melamine compound of claim 1, wherein R1 and R2 are independently a C6-C20 aryl or unsubstituted or substituted by an alkyl or an alkoxy; a C6-C20 aryloxy or unsubstituted or substituted by an alkyl or an alkoxy; or a dicyclopentadiene group.

3. The melamine compound of claim 1, wherein R1 is H and R2 is a phenyl unsubstituted or substituted by an alkyl or an alkoxy phenyl group.

4. A method for manufacturing melamine compound of formula I

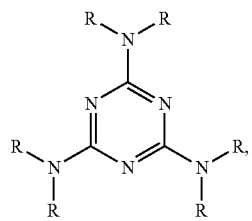

[Formula I]

comprising:
(a) reacting melamine with formaldehyde under a basic condition to provide a first solution;
(b) reacting the first solution with a phenolic compound of Formula Ia to provide a first intermediate:

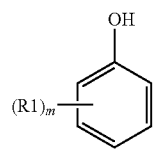

[Formula Ia]

(c) reacting the first intermediate with formaldehyde and a primary amine having a general formula of NH$_2$R2 to obtain the melamine compound, wherein,
R1 is independently selected from a group consisting of H; a C1-C15 alkyl unsubstituted or substituted by an alkyl or an alkoxy; a C1-C15 alkoxy or unsubstituted or substituted by an alkyl or an alkoxy; a C3-C15 cycloalkyl unsubstituted or substituted by an alkyl or an alkoxy; a C6-C20 aryl unsubstituted or substituted by an alkyl or an alkoxy; a C6-C20 aryloxy unsubstituted or substituted by an alkyl or an alkoxy; and a dicyclopentadiene group;

R2 is selected from a group consisting of a C1-C15 alkyl unsubstituted or substituted by an alkyl or an alkoxy; a C1-C15 alkoxy unsubstituted or substituted by an alkyl or an alkoxy; a C3-C15 cycloalkyl unsubstituted or substituted by an alkyl or an alkoxy; a C6-C20 aryl unsubstituted or substituted by an alkyl or an alkoxy; a C6-C20 aryloxy unsubstituted or substituted by an alkyl or an alkoxy; and a dicyclopentadiene group; and m is 1 or 2.

5. The method of claim 4, wherein R1 and R2 are independently a C6-C20 aryl unsubstituted or substituted by an alkyl or an alkoxy; a C6-C20 aryloxy unsubstituted or substituted by an alkyl or an alkoxy; or a dicyclopentadiene group.

6. The method of claim 4, wherein R1 is H and R2 is a phenyl unsubstituted or substituted by an alkyl or an alkoxy.

7. The method of claim 4, wherein step (a) is carried out at a pH value ranging from about 8 to about 10 and a temperature ranging from about 50° C. to about 75° C.

8. The method of claim 4, further comprising adjusting the first solution to neutral prior to carrying out step (b).

9. The method of claim 4, wherein step (b) further comprises mixing water with the product of reacting the first solution and the phenolic compound of Formula Ia to form an emulsion, and purifying and drying the emulsion to obtain the first intermediate.

10. The method of claim 4, wherein step (b) and step (c) are individually carried out at a temperature ranging from about 80° C. to about 95° C.

11. The method of claim 4, wherein step (c) is carried out in a solvent selected from a group consisting of dioxane, toluene, xylene, N,N-dimethyl formamide (DMF), N,N-dimethyl acetamide (DMAc), dimethyl sulfoxide (DMSO) and combinations thereof.

12. The method of claim 11, wherein step (c) comprises:
mixing the first intermediate with the solvent and the primary amine having a general formula of $NH_2R2$ to provide a first reaction mixture;
adding formaldehyde into the first reaction mixture and carrying out a reaction at a temperature ranging from about 80° C. to about 95° C. to obtain a solution containing the melamine compound; and
purifying and drying the solution to obtain the melamine compound.

* * * * *